(12) United States Patent
Mann et al.

(10) Patent No.: US 9,288,989 B2
(45) Date of Patent: Mar. 22, 2016

(54) SYNERGISTIC WEED CONTROL FROM APPLICATIONS OF PENOXSULAM AND ACETOCHLOR

(71) Applicant: Dow AgroSciences LLC, Indianapolis, IN (US)

(72) Inventors: Richard K. Mann, Franklin, IN (US); Nathalie Blanchier, Saint-Quentin-en-Yvelines (FR); Natalino Dalla Valle, Nove (IT); Dominique Larelle, Le Tremblay sur Mauldre (FR)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/188,447

(22) Filed: Feb. 24, 2014

(65) Prior Publication Data

US 2014/0243200 A1    Aug. 28, 2014

Related U.S. Application Data

(60) Provisional application No. 61/768,802, filed on Feb. 25, 2013.

(51) Int. Cl.
*A01N 43/90* (2006.01)
*A01N 37/26* (2006.01)

(52) U.S. Cl.
CPC ...................................... *A01N 43/90* (2013.01)

(58) Field of Classification Search
CPC ........ A01N 43/90; A01N 37/26; A01N 25/32
See application file for complete search history.

(56) References Cited

U.S. PATENT DOCUMENTS

| | | | |
|---|---|---|---|
| 5,858,924 | A | 1/1999 | Ehr et al. |
| 7,314,849 | B2 | 1/2008 | Balko et al. |
| 7,432,227 | B2 | 10/2008 | Balko et al. |
| 8,071,508 | B2 | 12/2011 | Keenan et al. |
| 2002/0055435 | A1 | 5/2002 | Baltruschat et al. |
| 2006/0167018 | A1 | 7/2006 | Zagar et al. |
| 2006/0183637 | A1 | 8/2006 | Loughner et al. |
| 2010/0099564 | A1 | 4/2010 | Hacker et al. |
| 2010/0279864 | A1 | 11/2010 | Mann et al. |
| 2011/0092367 | A1 | 4/2011 | Griveau et al. |
| 2011/0183845 | A1 | 7/2011 | Loughner et al. |
| 2011/0190134 | A1 | 8/2011 | Jousseaume et al. |
| 2011/0190135 | A1 | 8/2011 | Mann et al. |
| 2011/0190136 | A1 | 8/2011 | Hufnagl et al. |
| 2012/0284812 | A1 | 11/2012 | Mankin et al. |

FOREIGN PATENT DOCUMENTS

| | | |
|---|---|---|
| EP | 1313369 | 6/2005 |
| WO | 2012150333 | 11/2012 |

OTHER PUBLICATIONS

DuPont Breakfree ATZ label (2010).*
HCAPLUS abstract 2000:337879 (2000).*
Anonymous. "462055: 2-(2,2-difluoroethoxy)-6-trifluoromethyl-N-(5,8-dimethoxy[1,2,4]triazolo[1,5-c]pyrimidin-2-yl) benzenesulfonamide and its use as a herbicide in mixtures" Research Disclosure, Oct. 10, 2002, 4 pages.
Anonymous. "Penoxsulam and Its use as a Herbicide in Mixtures for use in Rice, Wheat, Barely, Oats, Sorghum, Corn, Maize, IVM, Rangeland, Pastures, Grasslands, Fallowland, Turf and Aquatics" IP.com Electronic Publication, IPCOM000116219D, Mar. 30, 2005, 15 pages.
"Product Safety Assessment: Penoxsulam" Dow Chemical Company, Sep. 23, 2008, 7 pages.
Relay Super 900 EC Label, Dow Agrosciences Southern Africa (PTY) LTD, Nov. 12, 2007, 32 pages.
Third Party Observation filed in PCT/US2014/018074, filed Sep. 10, 2014, 3 pages.
Farm Chemical International, Crop Protection Database, "Acetochlor," available at http://www.farmchemicalsinternational.com/crop-protection-database/#/product/detail/21780/ (accessed on May 27, 2014).
Farm Chemical International, Crop Protection Database, "Penoxsulam," available at http://www.farmchemicalsinternational.com/crop-protectiondatabase/#/product/detail/424174/ (accessed on May 27, 2014).
Tomlin, C. D. S., Ed., The Pesticide Manual: A World Compendium, "Acetochlor," 15th ed., BCPC: Alton, 2009, pp. 10-12.
Tomlin, C. D. S., Ed., The Pesticide Manual: A World Compendium, "Penoxsulam," 15th ed., BCPC: Alton, 2009, pp. 874-875.
International Search Report and Written Opinion issued May 21, 2014, in related International Patent Application No. PCT/US2014/018074.

* cited by examiner

*Primary Examiner* — John Pak
(74) *Attorney, Agent, or Firm* — Michael R. Asam; Meunier Carlin & Curfman LLC

(57) ABSTRACT

Disclosed herein are herbicidal compositions comprising a synergistic herbicidally effective amount of (a) penoxsulam or an agriculturally acceptable salt thereof and (b) acetochlor or an agriculturally acceptable salt thereof. Also disclosed herein are methods of controlling undesirable vegetation, which comprise applying to vegetation or an area adjacent the vegetation or applying to soil or water to prevent the emergence or growth of vegetation (a) penoxsulam or an agriculturally acceptable salt thereof and (b) acetochlor or an agriculturally acceptable salt thereof, wherein (a) and (b) are each added in an amount sufficient to produce a synergistic herbicidal effect.

14 Claims, No Drawings

SYNERGISTIC WEED CONTROL FROM APPLICATIONS OF PENOXSULAM AND ACETOCHLOR

CROSS REFERENCE TO RELATED APPLICATIONS

This application claims the benefit of U.S. Provisional Patent Application Ser. No. 61/768,802 filed Feb. 25, 2013, the disclosure of which is expressly incorporated herein by reference.

FIELD OF THE DISCLOSURE

The present disclosure relates to herbicidal compositions comprising a synergistic herbicidally effective amount of (a) penoxsulam or an agriculturally acceptable salt thereof and (b) acetochlor or an agriculturally acceptable salt thereof. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Herbicides of many types have been disclosed in the literature and a number are in commercial use. In some cases, herbicidal active ingredients have been found more effective in combination than when applied individually and this is referred to as "synergy" or "synergism." The present disclosure is based on the discovery that (a) penoxsulam or an agriculturally acceptable salt thereof and (b) acetochlor or an agriculturally acceptable salt thereof display a synergistic herbicidal effect when applied in combination.

Accordingly, the present disclosure relates to herbicidal compositions comprising a synergistic herbicidally effective amount of (a) penoxsulam or an agriculturally acceptable salt thereof and (b) acetochlor or an agriculturally acceptable salt thereof. The weight ratio of (a) to (b) can be from 1:2500 to 5:1 (e.g., from 1:460 to 1:1).

In some embodiments, the composition further comprises an additional pesticide (e.g., cyhalofop, haloxyfop, quizalofop, fenoxaprop, profoxydim, oxyfluorfen, triclopyr, fluroxypyr, atrazine, terbuthylazine, bensulfuron, clopyralid, flumetsulam, S-ethyl dipropylcarbamothioate (EPTC), metsulfuron, agriculturally acceptable salts or esters thereof, or combinations thereof). In some embodiments, the composition further comprises a herbicidal safener, an agriculturally acceptable adjuvant or carrier, or a combination thereof.

The present disclosure also relates to methods of controlling undesirable vegetation, which comprise applying to vegetation or an area adjacent the vegetation or applying to soil or water to prevent the emergence or growth of vegetation (a) penoxsulam or an agriculturally acceptable salt thereof and (b) acetochlor or an agriculturally acceptable salt thereof, wherein (a) and (b) are each applied in an amount sufficient to produce a synergistic herbicidal effect. In some embodiments, (a) and (b) are applied simultaneously. In some embodiments, (a) and (b) are applied pre-emergence of the undesirable vegetation.

The undesirable vegetation can be a broadleaf weed, a grass weed, a sedge weed, or combinations thereof. In some embodiments, the undesirable vegetation includes redroot pigweed, lambsquarters, swamp grass, cleavers, redshank, pale persicaria, black bindweed, black nightshade, field pansy, purple nutsedge, species of the genus *Tribulus*, or combinations thereof. The undesirable vegetation can be controlled in, for instance, cereals, citrus, coffee, corn, cotton, maize, onions, oilseed rape/canola, soybeans, sorghum, sugarbeets, sunflower, vineyards, rice, sugarcane, bearing and non-bearing tree nuts and orchards, grasses grown for seed, pastures, grasslands, rangelands, fallow land, rights-of-way, aquatic settings, tree and vine, ornamental species, or turfgrass.

In some embodiments, (a) is applied in an amount of from 2-50 grams of active ingredient per hectare (g ai/ha) (e.g., from 5-20 g ai/ha). In some embodiments, (b) is applied in an amount of from 10-5000 g ai/ha (e.g., from 15-2300 g ai/ha).

The description below sets forth details of one or more embodiments of the present disclosure. Other features, objects, and advantages will be apparent from the description and from the claims.

DETAILED DESCRIPTION

The present disclosure relates to herbicidal compositions comprising a synergistic herbicidally effective amount of (a) penoxsulam or an agriculturally acceptable salt thereof and (b) acetochlor or an agriculturally acceptable salt thereof. The present disclosure also relates to methods for controlling undesirable vegetation.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Penoxsulam

Compositions and methods of the present disclosure can include penoxsulam (i.e., 2-(2,2-difluoroethoxy)-N-(5,8-dimethoxy[1,2,4]triazolo[1,5-c]pyrimidin-2-yl)-6-trifluoromethyl)benzenesulfonamide) or an agriculturally acceptable salt thereof. Penoxsulam, shown below, is a triazolopyrimidine sulfonamide herbicide that provides broad-spectrum control of many annual, biannual, and perennial weeds. Penoxsulam, as well as methods of preparing penoxsulam, are known in the art. See, for example, U.S. Pat. No. 5,858,924 to Loughner et al.

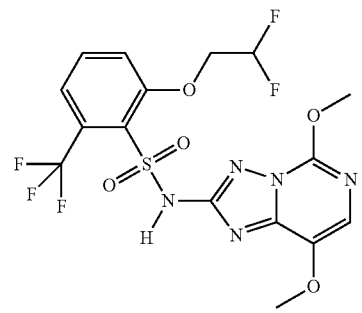 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam. Exemplary agriculturally acceptable salts of penoxsulam include, but are not limited to, sodium salts, potassium salts, ammonium salts or substituted ammonium salts, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts.

Penoxsulam can be used to control broadleaf weeds in, for instance, rice, corn, sorghum, wheat, barley and other cereal crops, lawns (e.g., residential, industrial, and institutional), golf courses, parks, cemeteries, athletic fields, sod farms, tree and vine crops, range and pasture, rights-of-way, roadsides, and other crop and non-crop uses. Its herbicidal activity is described in Tomlin, C. D. S., Ed. *The Pesticide Manual: A World Compendium,* 15th ed.; BCPC: Alton, 2009 (hereafter "The Pesticide Manual, Fifteenth Edition, 2009"). Penoxsulam is or has been commercially available, for example, from Dow AgroSciences LLC under the trademarks FENCER®, RICER®, VIPER®, CLIPPER®, SAPPHIRE®, GRASP®, and GRANITE® and from SePRO Corporation under the trademark GALLEON®.

Penoxsulam or an agriculturally acceptable salt thereof can be applied to vegetation or an area adjacent the vegetation or applied to soil or water to prevent the emergence or growth of vegetation in an amount sufficient to induce a herbicidal effect. In some embodiments, the penoxsulam or agriculturally acceptable salt thereof is applied to vegetation or an area adjacent the vegetation or applied to soil or water to prevent the emergence or growth of vegetation in an amount of 2 grams or greater of active ingredient per hectare (g ai/ha) (e.g., 3 g ai/ha or greater, 4 g ai/ha or greater, 5 g ai/ha or greater, 7.5 g ai/ha or greater, 10 g ai/ha or greater, 15 g ai/ha or greater, 20 g ai/ha or greater, 25 g ai/ha or greater, 30 g ai/ha or greater, 35 g ai/ha or greater, 40 g ai/ha or greater, or 45 g ai/ha or greater). In some embodiments, the penoxsulam or agriculturally acceptable salt thereof is applied to vegetation or an area adjacent the vegetation or applied to soil or water to prevent the emergence or growth of vegetation in an amount of 50 g ai/ha or less (e.g., 45 g ai/ha or less, 40 g ai/ha or less, 35 g ai/ha or less, 30 g ai/ha or less, 25 g ai/ha or less, 20 g ai/ha or less, 15 g ai/ha or less, 10 g ai/ha or less, 7.5 g ai/ha or less, 5 g ai/ha or less, 4 g ai/ha or less, or 3 g ai/ha or less).

Penoxsulam can be applied to vegetation or an area adjacent the vegetation or applied to soil or water to prevent the emergence or growth of vegetation in an amount ranging from any of the minimum values described above to any of the maximum values described above. In some embodiments, the penoxsulam or agriculturally acceptable salt thereof is applied to vegetation or an area adjacent the vegetation or applied to soil or water to prevent the emergence or growth of vegetation in an amount of from 2-50 g ai/ha (e.g., from 2.5-40 g ai/ha, from 3-30 g ai/ha, from 4-25 g ai/ha, or from 5-20 g ai/ha).

Acetochlor

Compositions and methods of the present disclosure can include acetochlor or an agriculturally acceptable salt thereof. Acetochlor (i.e., 2-chloro-N-(ethoxymethyl)-N-(2-ethyl-6-methylphenyl)acetamide), shown below, is a chloroacetamide herbicide that can be used to control annual grasses and broadleaf weeds in, for instance, in cabbage, citrus, coffee, corn, cotton, green peas, maize, onions, orchards, soybeans, sugar beets, sunflower, and vineyards. Its herbicidal activity is described in *The Pesticide Manual*, Fifteenth Edition, 2009.

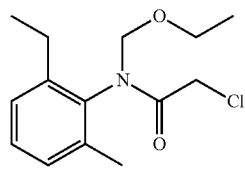 [SMILES: CCOCN(C(=O)CCl)c1c(C)cccc1CC]

Acetochlor is or has been commercially available, for example, under the trademarks SURPASS® (by Dow AgroSciences LLC), TOPNOTCH® (by Dow AgroSciences LLC), TROPHY® (by Dow AgroSciences LLC), RELAY® (by Dow AgroSciences LLC), BREAKFREE® (by DuPont Crop Protection), XINCHLOR® (by Jiangsu Xinyi Pesticide Ltd.), ACENIT® (by Makhteshim Agan Group), ACETO-GAN® (by Makhteshim Agan Group), FIRST ACT® (by Makhteshim Agan Group), NITRIGUARD® (by Makhteshim Agan Group), DEGREE® (by Monsanto Co.), HARNESS® (by Monsanto Co.), WARRANT® (by Monsanto Co.), PILARPASS® (by Pilar AgriScience Corp.), EAGROW® (by Shandong Kesai Eagrow Co., Ltd.), ASER® (by Wangs Crop-Science Co., Ltd.), and COME TRUE® (by Wangs Crop-Science Co., Ltd.).

The acetochlor or an agriculturally acceptable salt thereof can be used in an amount sufficient to induce a herbicidal effect. In some embodiments, the acetochlor or agriculturally acceptable salt thereof is applied to vegetation or an area adjacent the vegetation or applied to soil or water to prevent the emergence or growth of vegetation in an amount of 10 grams of active ingredient per hectare (g ai/ha) or greater (e.g., 15 g ai/ha or greater, 20 g ai/ha or greater, 25 g ai/ha or greater, 30 g ai/ha or greater, 40 g ai/ha or greater, 50 g ai/ha or greater, 75 g ai/ha or greater, 100 g ai/ha or greater, 150 g ai/ha or greater, 200 g ai/ha or greater, 250 g ai/ha or greater, 300 g ai/ha or greater, 400 g ai/ha or greater, 500 g ai/ha or greater, 600 g ai/ha or greater, 700 g ai/ha or greater, 750 g ai/ha or greater, 800 g ai/ha or greater, 900 g ai/ha or greater, 1000 g ai/ha or greater, 1100 g ai/ha or greater, 1200 g ai/ha or greater, 1250 g ai/ha or greater, 1300 g ai/ha or greater, 1400 g ai/ha or greater, 1500 g ai/ha or greater, 1600 g ai/ha or greater, 1700 g ai/ha or greater, 1750 g ai/ha or greater, 1800 g ai/ha or greater, 1900 g ai/ha or greater, 2000 g ai/ha or greater, 2100 g ai/ha or greater, 2200 g ai/ha or greater, 2250 g ai/ha or greater, 2300 g ai/ha or greater, 2400 g ai/ha or greater, 2500 g ai/ha or greater, 2750 g ai/ha or greater, 3000 g ai/ha or greater, 3250 g ai/ha or greater, 3500 g ai/ha or greater, 3750 g ai/ha or greater, 4000 g ai/ha or greater, 4250 g ai/ha or greater, 4500 g ai/ha or greater, or 4750 g ai/ha or greater). In some embodiments, the acetochlor or agriculturally acceptable salt thereof is applied to vegetation or an area adjacent the vegetation or applied to soil or water to prevent the emergence or growth of vegetation in an amount of 5000 g ai/ha or less (e.g., 4750 g ai/ha or less, 4500 g ai/ha or less, 4250 g ai/ha or less, 4000 g ai/ha or less, 3750 g ai/ha or less, 3500 g ai/ha or less, 3250 g ai/ha or less, 3000 g ai/ha or less, 2750 g ai/ha or less, 2500 g ai/ha or less, 2400 g ai/ha or less, 2300 g ai/ha or less, 2250 g ai/ha or less, 2200 g ai/ha or less, 2100 g ai/ha or less, 2000 g ai/ha or less, 1900 g ai/ha or less, 1800 g ai/ha or less, 1750 g ai/ha or less, 1700 g ai/ha or less, 1600 g ai/ha or less, 1500 g ai/ha or less, 1400 g ai/ha or less, 1300 g ai/ha or less, 1250 g ai/ha or less, 1200 g ai/ha or less, 1100 g ai/ha or less, 1000 g ai/ha or less, 900 g ai/ha or less, 800 g ai/ha or less, 750 g ai/ha or less, 700 g ai/ha or less, 600 g ai/ha or less, 500 g ai/ha or less, 400 g ai/ha or less, 300 g ai/ha or less, 250 g ai/ha or less, 200 g ai/ha or less, 150 g ai/ha or less, 100 g ai/ha or less, 75 g ai/ha or less, 50 g ai/ha or less, 40 g ai/ha or less, 30 g ai/ha or less, 25 g ai/ha or less, 20 g ai/ha or less, or 15 g ai/ha or less).

Acetochlor can be applied to vegetation or an area adjacent the vegetation or applied to soil or water to prevent the emergence or growth of vegetation in an amount ranging from any of the minimum values described above to any of the maximum values described above. In some embodiments, the acetochlor or agriculturally acceptable salt thereof is applied to vegetation or an area adjacent the vegetation or applied to soil or water to prevent the emergence or growth of vegetation in an amount of from 10-5000 g ai/ha (e.g., from 12.5-4500 g ai/ha, from 15-4300 g ai/ha, from 15-3800 g ai/ha, from 15-3300 g ai/ha, from 15-2800 g ai/ha, or from 15-2300 g ai/ha).

Herbicidal Mixtures or Combinations

The (a) penoxsulam or an agriculturally acceptable salt thereof is mixed with or applied in combination with (b) acetochlor or an agriculturally acceptable salt thereof in an amount sufficient to induce a synergistic herbicidal effect. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations, Weeds* 1967, 15, 20-22

$$E = X + Y - \left(\frac{X*Y}{100}\right)$$

wherein

X=effect in percent using (a) penoxsulam or an agriculturally acceptable salt thereof at an application rate a;

Y=effect in percent using (b) acetochlor or an agriculturally acceptable salt thereof at an application rate b;

E=expected effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of penoxsulam or an agriculturally acceptable salt thereof and acetochlor or an agriculturally acceptable salt thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the weight ratio of (a) penoxsulam or agriculturally acceptable salt thereof to (b) acetochlor or an agriculturally acceptable salt thereof that is sufficient to induce a synergistic herbicidal effect is at least 1:2500 (e.g., at least 1:2250, at least 1:2000, at least 1:1750, at least 1:1500, at least 1:1250, at least 1:1000, at least 1:750, at least 1:700, at least 1:600, at least 1:500, at least 1:450, at least 1:400, at least 1:380, at least 1:360, at least 1:350, at least 1:340, at least 1:320, at least 1:300, at least 1:280, at least 1:260, at least 1:250, at least 1:240, at least 1:220, at least 1:200, at least 1:180, at least 1:160, at least 1:150, at least 1:140, at least 1:120, at least 1:100, at least 1:80, at least 1:75, at least 1:70, at least 1:60, at least 1:50, at least 1:45, at least 1:40, at least 1:35, at least 1:30, at least 1:25, at least 1:20, at least 1:15, at least 1:10, at least 1:9, at least 1:8, at least 1:7, at least 1:6, at least 1:5, at least 1:4, at least 1:3, at least 1:2, at least 1:1, at least 5:4, at least 4:3, at least 3:2, at least 2:1, at least 5:2, at least 3:1, at least 7:2, at least 4:1, or at least 9:2). In some embodiments, the weight ratio of (a) to (b) that is sufficient to induce a synergistic herbicidal effect is 5:1 or less (e.g., 9:2 or less; 4:1 or less, 7:2 or less, 3:1 or less, 5:2 or less, 2:1 or less, 3:2 or less, 4:3 or less, 5:4 or less, 1:1 or less, 1:2 or less, 1:3 or less, 1:4 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:75 or less, 1:80 or less, 1:90 or less, 1:100 or less, 1:120 or less, 1:140 or less, 1:150 or less, 1:160 or less, 1:180 or less, 1:200 or less, 1:220 or less, 1:240 or less, 1:250 or less, 1:260 or less, 1:280 or less, 1:300 or less, 1:320 or less, 1:340 or less, 1:350 or less, 1:360 or less, 1:380 or less, 1:400 or less, 1:450 or less, 1:500 or less, 1:600 or less, 1:700 or less, 1:750 or less, 1:1000 or less, 1:1250 or less, 1:1500 or less, 1:1750 or less, 1:2000 or less, or 1:2250 or less).

The weight ratio of (a) penoxsulam or agriculturally acceptable salt thereof to (b) acetochlor or an agriculturally acceptable salt thereof that is sufficient to induce a synergistic herbicidal effect can range from any of the minimum ratios described above to any of the maximum values described above. In some embodiments, the weight ratio of (a) penoxsulam or agriculturally acceptable salt thereof to (b) acetochlor or an agriculturally acceptable salt thereof that is sufficient to induce a synergistic herbicidal effect is from 1:2500 to 5:1 (e.g., from 1:2000 to 4:1, from 1:1000 to 7:2, from 1:800 to 3:1, from 1:600 to 5:2, from 1:500 to 2:1, 1:460 to 1:1, from 1:400 to 3:2, or from 1:360 to 4:3).

Formulations

The present disclosure also relates to formulations of the compositions and methods disclosed herein. In some embodiments, the formulation can be in the form of a single package formulation including both (a) penoxsulam or an agriculturally acceptable salt thereof and (b) acetochlor or an agriculturally acceptable salt thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) penoxsulam or an agriculturally acceptable salt thereof and/or (b) acetochlor or an agriculturally acceptable salt thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the penoxsulam or agriculturally acceptable salt thereof. In some embodiments, the additive is premixed with the acetochlor or agriculturally acceptable salt thereof. In some embodiments, the additive is premixed with the penoxsulam or agriculturally acceptable salt thereof and the acetochlor or agriculturally acceptable salt thereof.

In some embodiments, the additive is an additional pesticide. For example, the compositions described herein can be applied in conjunction with one or more additional herbicides to control undesirable vegetation. The composition can be formulated with the one or more additional herbicides, tank-mixed with the one or more additional herbicides, or applied sequentially with the one or more additional herbicides. Exemplary additional herbicides include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, fluroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocard, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac-methyl, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfuron-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor and salts, esters, optically active isomers, and mixtures thereof.

In certain embodiments, the additional pesticide includes cyhalofop (e.g., cyhalofop-butyl), haloxyfop, quizalofop (e.g., quizalofop-P-ethyl), fenoxaprop, profoxydim, oxyfluorfen, triclopyr, fluroxypyr, atrazine, terbuthylazine, bensulfuron (e.g., bensulfuron-methyl), clopyralid, flumetsulam, S-ethyl dipropylcarbamothioate (EPTC), metsulfuron (e.g., metsulfuron-methyl), and agriculturally acceptable salts or esters thereof, or combinations thereof.

In some embodiments, the penoxsulam or an agriculturally acceptable salt thereof is provided in a premixed formulation with an additional pesticide. In some embodiments, the penoxsulam or an agriculturally acceptable salt thereof is premixed with, cyhalofop-butyl, oxyfluorfen, triclopyr, or combinations thereof. Exemplary premixes of penoxsulam or an agriculturally acceptable salt or ester thereof and an additive that are or have been commercially available include, but are not limited to, CLINTON® (a premix incorporating cyhalofop-butyl by Dow AgroSciences LLC), REBEL EX™ (a premix incorporating cyhalofop-butyl by Dow AgroSciences LLC), RICER® (a premix incorporating cyhalofop-butyl by Dow AgroSciences LLC), PINDAR GT® (a premix incorporating oxyfluorfen by Dow AgroSciences LLC), and GRASP® XTRA (a premix incorporating triclopyr by Dow AgroSciences LLC).

In some embodiments, the acetochlor or an agriculturally acceptable salt thereof is provided in a premixed formulation with an additional pesticide. In some embodiments, the acetochlor or an agriculturally acceptable salt thereof is premixed with atrazine, terbuthylazine, bensulfuron-methyl, clopyralid, flumetsulam, S-ethyl dipropylcarbamothioate (EPTC), flurochloridone, metsulfuron-methyl, quizalofop-P-ethyl, or combinations thereof. Exemplary premixes of acetochlor or an agriculturally acceptable salt thereof and an additive that are or have been commercially available include, but are not limited to, BREAKFREE ATZ® (a premix incorporating atrazine by DuPont Crop Protection), BREAKFREE ATZ LITE® (a premix incorporating atrazine by DuPont Crop Protection), CADENCE ATZ® (a premix incorporating atrazine by Loveland Products, Inc.), CADENCE ATZ LITE® (a premix incorporating atrazine by Loveland Products, Inc.), CONFIDENCE XTRA® (a premix incorporating atrazine by Winfield Solutions, LLC), DEGREE XTRA® (a premix incorporating atrazine by Monsanto Co.), DOUBLE TEAM® (a premix incorporating atrazine by Makhteshim Agan Group), FULTIME® (a premix incorporating atrazine by Dow AgroSciences LLC), HARNESS XTRA® (a premix incorporating atrazine by Monsanto Co.), KEYSTONE® (a premix incorporating atrazine by Dow AgroSciences LLC), KEYSTONE LA® (a premix incorporating atrazine by Dow AgroSciences LLC), SIGMA COMBI® (a premix incorporating atrazine by Willowood Ltd.), RIVAL® (a premix incorporating atrazine and terbuthylazine by Meridian Agrochemical Pty. Ltd. t/a Meridian Agritech), LONG GENG® (a premix incorporating bensulfuron-methyl by Shanghai Agro-Chemical Industry Co., Ltd.), SURESTART® (a premix incorporating clopyralid and flumetsulam by Dow AgroSciences LLC), TRIPLEFLEX® (a premix incorporating clopyralid and flumetsulam by Monsanto Co.), IMPERIUM® (a premix incorporating EPTC by Gowan Company), TWINPACK® (a premix incorporating flurochloridone by Makhteshim Agan Group), MIECAOBAO® (a premix incorporating metsulfuron-methyl by Guangxi Beihai Penshibao Co., Ltd.), YANGFU+YICAO AN® (a premix incorporating oxyfluorfen by Nanjing Red Sun Co., Ltd.), SHUANG CAO JINGO (a premix incorporating quizalofop-P-ethyl by Shanghai Agro-Chemical Industry Co., Ltd.)

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, $C_9$-$C_{11}$ alkylpolyglycoside or less, phosphate alcohol ethoxylate or less, natural primary alcohol ($C_{12}$-$C_{16}$) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG(400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, R29148, and N-phenyl-sulfonylbenzoic acid amides, as well as agriculturally acceptable salts and, provided they have a carboxyl group, their agriculturally acceptable derivatives thereof.

In some embodiments, the safener can be cloquintocet or an ester or salt thereof, such as cloquintocet (mexyl). In some embodiments, the safener can be dichlormid. In some embodiments, the safener is employed in rice, cereal, corn, or maize. For example, dichlormid or cloquintocet can be used to antagonize harmful effects of the compositions on rice, row crops, and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

Methods of Application

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). The compositions can be applies as an in-water application (e.g., to a flooded paddy rice or body of water).

When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil or water to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action. In some cases, the compositions are applied to relatively immature undesirable vegetation.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, cereals, citrus, coffee, corn, cotton, maize, onions, oilseed rape/canola, soybeans, sorghum, sugar beets, sunflower, vineyards, rice, sugarcane, bearing and non-bearing tree nuts and orchards, grasses grown for seed, and ornamental species. In some embodiments, the undesirable vegetation is controlled in a row crop (e.g., corn, sorghum, soybean, cotton, or oilseed rape/canola). In certain embodiments, the compositions and methods disclosed herein can be used for controlling undesired vegetation in corn. In certain embodiments, the compositions and methods disclosed herein can be used for controlling undesired vegetation in sorghum. In certain embodiments, the compositions and methods provided herein are utilized to control undesirable vegetation in rice (e.g., direct-seeded, water-seeded, or transplanted rice).

The compositions and methods disclosed herein can be used for controlling undesired vegetation in non-crop areas. Exemplary non-crop areas include, but are not limited to, turfgrass, pastures, grasslands, rangelands, fallow land, rights-of-way, aquatic settings, tree and vine, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, cereals, citrus, coffee, corn, cotton, maize, onions, oilseed rape/canola, soybeans, sorghum, sugar beets, sunflower, vineyards, rice, sugarcane, bearing and non-bearing tree nuts and orchards, grasses grown for seed, tree and vine, ornamental species, and turfgrass that are resistant to synthetic auxins, or crop plants that, owing to introduction of the gene for *Bacillus thuringiensis* (or Bt) toxin by genetic modification, are resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant crops possessing multiple or stacked traits conferring tolerance to multiple chemistries and/or multiple modes-of-action. The combination of (a), (b), and a complementary herbicide or salt or ester thereof can be used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or as sequential applications.

The herbicidal compositions prepared disclosed herein are effective against a variety of types of undesirable vegetation. In some embodiments, the compositions disclosed herein can be used for controlling broadleaf weeds, grass weeds, sedge weeds, and combinations thereof.

In some embodiments, the compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (Fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SCPJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (Western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, the compositions and methods provided herein are utilized to control undesirable vegetation consisting of grass, broadleaf and sedge weeds. In certain embodiments, the compositions and methods provided herein are utilized to control undesirable grass, broadleaf and sedge vegetation including but not limited to *Amaranthus, Chenopodium, Cyperus, Echinochloa, Galium, Polygonum, Solanum, Tribulus* and *Viola*. In certain cases, the undesirable vegetation is selected from redroot pigweed (*Amaranthus retroflexus*), lambsquarter (*Chenopodium album*), field pansy (*Viola arvensis*), junglerice (*Echinochloa colonum*), cleavers (*Galium aparine*), wild buckwheat (*Polygonum convolvulus* L.), pale smartweed (*Polygonum lapathifolium* L.), ladysthumb (*Polygonum persicaria* L.), black nightshade (*Solanum nigrum*), purple nutsedge (*Cyperus rotundus*), species of the genus *Tribulus*, (e.g., common caltrop (*Tribulus terrestris*), spineless caltrop (*Tribulus micrococcus*), Jamaican fever plant (*Tribulus cistoides*), and devil-thorn weed (*Tribulus zeyheri*)), or combinations thereof.

The compositions and methods provided herein can be used to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

By way of non-limiting illustration, examples of certain embodiments of the present disclosure are given below.

EXAMPLES

Evaluation of Pre-Emergence Applications of Penoxsulam and Acetochlor for Synergistic Weed Control Field trials were conducted with applications made in the area of naturally occurring weed populations in multiple countries. The soil or water was treated prior to the emergence of target plants. All treatments were applied using a randomized complete block trial design, with 3-5 replications per treatment.

Treatments consisted of penoxsulam and acetochlor applied alone and in combination. Spray solutions were prepared using an appropriate amount of dilution to treat the area of the plots based on use rates and water volumes necessary based on a per hectare basis. Spray solutions were prepared and applied with the specified active ingredients in single and two-way combinations to be able to perform Colby synergy and safening calculations. Formulated products were applied to the soil with a backpack sprayer equipped with flat fan nozzles calibrated to deliver from 200 to 300 L/ha at a normal spray height above the soil, at spray pressures ranging from 200 to 400 kilopascals (kPa). Formulated products were applied into flooded rice paddy by calculating the area to be treated, calculating the amount of active ingredient necessary to treat the area at the specified rates, then mixing the treatments in water to apply 8 L/ha of water to the plots.

Colby's equation was used to determine the herbicidal effects expected from the mixtures, as described above. The results were measured at the evaluation intervals provided in Table 1 after the first application of the compositions. The trials exhibited unexpected synergy, and those results were found statistically significant under the p-value test. The herbicide tank-mix combinations tested, application rates and ratios employed, plant species tested, and results are given below.

TABLE 1

Synergistic Weed Control from Applications of Penoxsulam + Acetochlor.

| | | Penoxsulam | | Acetochlor | | Combination | |
|---|---|---|---|---|---|---|---|
| Weed Bayer | Evaluation Interval | g ai/ha | Mean % weed control | g ai/ha | Mean % weed control | Measured mean % weed control | Colby predicted mean % weed control |
| AMARE | 55 days | 12 | 30 | 2000 | 0 | 89.33 | 30 |
| CHEAL | 34 days | 20 | 56.67 | 1400 | 3.33 | 93.33 | 58 |

TABLE 1-continued

Synergistic Weed Control from Applications of Penoxsulam + Acetochlor.

| | | Penoxsulam | | Acetochlor | | Combination | |
|---|---|---|---|---|---|---|---|
| Weed Bayer | Evaluation Interval | g ai/ha | Mean % weed control | g ai/ha | Mean % weed control | Measured mean % weed control | Colby predicted mean % weed control |
| CHEAL | 61 days | 20 | 50 | 1400 | 36.67 | 95.33 | 69 |
| VIOAR | 61 days | 20 | 0 | 1400 | 0 | 100 | 0 |
| GALAP | 38 days | 20 | 40 | 1900 | 6.67 | 81.67 | 44 |
| GALAP | 64 days | 20 | 60 | 1900 | 10 | 88.33 | 64.33 |
| SOLNI | 64 days | 20 | 40 | 1900 | 13.33 | 76.67 | 48.33 |
| SOLNI | 92 days | 20 | 30 | 1900 | 3.33 | 70 | 32.33 |
| ECHCO | 20 days | 15 | 38.75 | 15 | 22.5 | 78.75 | 52.5 |
| ECHCO | 20 days | 20 | 50 | 15 | 22.5 | 87.5 | 61.25 |
| ECHCO | 35 days | 15 | 55 | 15 | 15 | 81.25 | 61.75 |
| CYPRO | 35 days | 20 | 39.38 | 15 | 4.25 | 56.25 | 41.93 |
| TRBSS | 35 days | 10 | 38.5 | 1800 | 78 | 98 | 86.78 |
| TRBSS | 35 days | 5 | 32 | 1800 | 78 | 100 | 85.2 |
| TRBSS | 49 days | 10 | 32 | 1800 | 63 | 97 | 75.53 |
| TRBSS | 49 days | 5 | 13 | 1800 | 63 | 100 | 67.7 |
| POLPE | 14 days | 20 | 80 | 1400 | 36.67 | 96 | 87.17 |
| POLCO | 14 days | 15 | 85 | 2300 | 5 | 97.5 | 86 |
| POLLA | 14 days | 15 | 85 | 2300 | 20 | 100 | 87.5 |
| POLCO | 28 days | 15 | 65 | 2300 | 5 | 98.75 | 67 |
| POLLA | 28 days | 15 | 75 | 2300 | 10 | 100 | 77 |
| POLLA | 98 days | 15 | 71.25 | 2300 | 12.5 | 95.62 | 74 |
| POLCO | 14 days | 20 | 87.5 | 2300 | 27.5 | 100 | 91.5 |
| POLLA | 28 days | 20 | 90 | 2300 | 7.5 | 98.75 | 91 |
| POLCO | 28 days | 20 | 77.5 | 2300 | 12.5 | 100 | 80.75 |

As shown above, the weed control from the treatments in these trials demonstrated synergistic weed control, with higher measured weed control than would be predicted by the Colby equation.

Crop Safening Results on *Sorghum* and Corn from Pre-Emergence Application of Penoxsulam and Acetochlor Field trials were conducted with applications made to the soil prior to the emergence of the crops. All treatments were applied using a randomized complete block trial design, with 4 replications per treatment.

Treatments consisted of penoxsulam and acetochlor, applied alone or in combination. Spray solutions were prepared using an appropriate amount of dilution to treat the area of the plots based on use rates and water volumes necessary based on a per hectare basis. Spray solutions were prepared and applied with the specified active ingredients in single and two-way combinations to be able to perform Colby synergy and safening calculations. Formulated products were applied to the soil with a backpack sprayer equipped with flat fan nozzles calibrated to deliver from 200 to 300 L/ha at a normal spray height above the soil, at spray pressures ranging from 200 to 400 kilopascals (kPa). Formulated products were applied by calculating the area to be treated, calculating the amount of active ingredient necessary to treat the area at the specified rates, then mixing the treatments in water to apply 8 L/ha of water to the crop plots. Data for sorghum (SORVU) and corn (ZEAMX) are provided in Table 2 below. The treated plots and control plots were rated blind at various intervals after application. Ratings were based on a scale of 0-100%, as discussed above, wherein 0% indicates no injury to the crop and 100% indicates complete control of the crop.

Colby's equation was used to determine the herbicidal effects expected from the mixtures, as described above. The results were measured at the evaluation intervals provided in Table 2 after the first application of the compositions. The trials exhibited unexpected synergy, and those results were found statistically significant under the p-value test. The herbicide tank mix combinations tested, application rates and ratios employed, plant species tested, and results are given below.

TABLE 2

Synergistic Crop Safening from Applications of Penoxsulam + Acetochlor.

| | | Penoxsulam | | Acetochlor[1] | | Combination | |
|---|---|---|---|---|---|---|---|
| Crop Bayer | Evaluation Interval | g ai/ha | Mean % crop injury | g ai/ha | Mean % crop injury | Measured mean % crop injury | Colby predicted mean % crop injury |
| SORVU | 6 days | 16 | 6.33 | 1400 | 5 | 7 | 11.02 |
| SORVU | 6 days | 16 | 6.33 | 2000 | 6.33 | 8.33 | 12.27 |
| SORVU | 9 days | 32 | 17.5 | 4000 | 18.75 | 21.25 | 32.94 |
| SORVU | 3 days | 32 | 23 | 4000 | 8.5 | 23.75 | 29.55 |
| ZEAMX | 98 days | 15 | 10 | 2300 | 0 | 0 | 10 |
| ZEAMX | 98 days | 15 | 20 | 2300 | 0 | 0.62 | 20 |
| ZEAMX | 14 days | 20 | 11.25 | 2300 | 0 | 3.75 | 11.25 |
| ZEAMX | 14 days | 20 | 17.5 | 2300 | 0 | 11.88 | 17.5 |
| ZEAMX | 28 days | 20 | 6.25 | 2300 | 0 | 0.62 | 6.25 |
| ZEAMX | 28 days | 20 | 17.5 | 2300 | 0 | 5 | 17.5 |

TABLE 2-continued

Synergistic Crop Safening from Applications of Penoxsulam + Acetochlor.

| Crop Bayer | Evaluation Interval | Penoxsulam | | Acetochlor[1] | | Combination | |
| --- | --- | --- | --- | --- | --- | --- | --- |
| | | g ai/ha | Mean % crop injury | g ai/ha | Mean % crop injury | Measured mean % crop injury | Colby predicted mean % crop injury |
| ZEAMX | 98 days | 20 | 6.25 | 2300 | 0 | 0 | 6.25 |
| ZEAMX | 98 days | 20 | 25 | 2300 | 0 | 3.12 | 25 |

[1]In some examples, acetochlor was provided as a commercial product that included acetochlor in combination with dichlormid.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a herbicidal mixture consisting of a synergistic herbicidally effective amount of (a) penoxsulam or an agriculturally acceptable salt thereof and (b) acetochlor or an agriculturally acceptable salt thereof, wherein the weight ratio of (a) to (b) is from 1:460 to 1:1.

2. The composition of claim 1, further comprising a herbicide safener.

3. The composition of claim 2, wherein the herbicide safener is selected from the group consisting of dichlormid, cloquintocet-mexyl, and combinations thereof.

4. A method of controlling undesirable vegetation which comprises applying to vegetation or an area adjacent the vegetation or applying to soil or water to control the emergence or growth of vegetation a herbicidal mixture consisting of a synergistic herbicidally effective amount of (a) penoxsulam or an agriculturally acceptable salt thereof and (b) acetochlor or an agriculturally acceptable salt thereof,
wherein (a) and (b) are applied in a weight ratio of (a) to (b) from 1:460 to 1:1,
and
wherein (a) is applied in an amount of from 5-20 g ai/ha and (b) is applied in an amount of from 15-2300 g ai/ha.

5. The method of claim 4, wherein (a) and (b) are applied simultaneously.

6. The method of claim 4, further comprising applying a herbicide safener.

7. The method of claim 6, wherein the herbicide safener is selected from the group consisting of dichlormid, cloquintocet-mexyl, and combinations thereof.

8. The method of claim 4, wherein the undesirable vegetation is controlled in cereals, citrus, coffee, corn, cotton, maize, onions, oilseed rape/canola, soybeans, sorghum, sugar beets, sunflower, vineyards, rice, sugarcane, bearing and non-bearing tree nuts and orchards, grasses grown for seed, pastures, grasslands, rangelands, fallow land, rights-of-way, aquatic settings, tree and vine, ornamental species, or turfgrass.

9. The method of claim 8, wherein the undesirable vegetation is controlled in rice.

10. The method of claim 8, wherein the undesirable vegetation is controlled in sorghum.

11. The method of claim 8, wherein the undesirable vegetation is controlled in corn.

12. The method of claim 4, wherein the undesirable vegetation includes a broadleaf weed, a grass weed, a sedge weed, or a combination thereof.

13. The method of claim 4, wherein the undesirable vegetation comprises a herbicide resistant or tolerant weed.

14. The method of claim 4, wherein the undesirable vegetation includes redroot pigweed, lambsquarter, field pansy, junglerice, cleavers, wild buckwheat, pale smartweed, ladysthumb, black nightshade, purple nutsedge, species of the genus *Tribulus*, and combinations thereof.

* * * * *